United States Patent [19]

Lawhorn

[11] Patent Number: 4,854,869

[45] Date of Patent: Aug. 8, 1989

[54] UNILATERAL DIRECTION CONTROL FOR DENTAL SYRINGE

[76] Inventor: Timothy M. Lawhorn, 626 Whitaker, Missoula, Mont. 59803

[21] Appl. No.: 99,082

[22] Filed: Sep. 21, 1987

[51] Int. Cl.[4] ............................................ A61G 17/02
[52] U.S. Cl. ........................................................ 433/80
[58] Field of Search ................ 433/80, 84, 85, 88, 433/130, 141; 128/66

[56] References Cited

U.S. PATENT DOCUMENTS

| | | | |
|---|---|---|---|
| 1,958,332 | 5/1934 | Carpenter | 433/80 |
| 2,066,313 | 1/1937 | Barr | 433/80 |
| 3,393,676 | 7/1968 | Kummer et al. | 433/80 |
| 3,452,745 | 7/1969 | Hutchinson et al. | 128/66 |
| 3,465,751 | 9/1969 | Powers | 128/66 |
| 3,511,235 | 5/1970 | Stram | 433/80 |
| 4,026,025 | 5/1977 | Hunt | 433/80 |
| 4,214,871 | 7/1980 | Arnold | 433/88 |
| 4,227,878 | 10/1980 | Lohn | 433/80 |
| 4,248,589 | 2/1981 | Lewis | 433/80 |
| 4,531,912 | 7/1985 | Schuss et al. | 433/80 |
| 4,619,612 | 10/1986 | Weber et al. | 433/80 |

Primary Examiner—John J. Wilson

[57] ABSTRACT

The present invention discloses a method for rotation of the nozzle of a dental syringe wherein that syringe is used to direct and deliver various agents including air and water. This method for rotation is facilitated by placement of an easily grasped component on the above mentioned nozzle. That easily grasped component is designed for use by the hand holding and operating that syringe while allowing that operating hand to remain in an operating position. The above mentioned component is fabricated separately from the above mentioned nozzle and subsequently attached to that otherwise functionally and aesthetically complete nozzle either temporarily or permanently. The present invention therefore provides for unilateral control over the direction, in relation to the handle of the syringe, of the agents as those agents exit that syringe. The present invention can be specifically designed for use on any such dental syringe, and can be provided as an initial aspect of the syringe nozzle or as an aftermarket addition.

3 Claims, 2 Drawing Sheets

UNILATERAL DIRECTION CONTROL FOR DENTAL SYRINGE

BACKGROUND

1. Field of Invention

This invention relates to control over the direction of the exit path of agents delivered from a dental syringe wherein that dental syringe is used to direct and deliver controlled amounts of various agents including air and water.

2. Discussion of Prior Art

Dental syringes for delivery of controlled amounts of various agents including air and water are present in the prior art. Examples can be seen by referring to U.S. Pat. Nos. 4,619,612; 4.531,912; 4,248,589; 4,227,878; 4,026,025; 3,511,235; 3,393,676; and 2,066,313 which demonstrate various designs of these syringes. The syringes mentioned above are hand held devices for use during delivery of dental care. These syringes allow the user to control the selection of agent or agents, the quantity of the desired agent or agents, and the direction of the exit path of the selected agent or agents in relation to the handle of that syringe.

In all but one instance, control over the exit path direction requires the use of both hands. To redirect the exit path the user of that syringe must use one hand to hold the syringe handle and the other hand to grasp the nozzle and rotate that nozzle in its connection with the syringe. It is rotation of the nozzle in that connection which alters the direction of the exit path.

Only the most current design, that disclosed in U.S. Pat. No. 4,619,612 provides for exit path direction control by the hand user to hold and operate the syringe under discussion. There is no mention of this advantage in the patent document other than the fact that its presence is demonstrated in the drawings as an enlarged area on the nozzle adjacent to the syringe head. In production of this design the ability to control exit path direction with the operating hand is facilitated by placement of a grasping means, in the area mentioned above, which is within reach of the operating hand and is used by that hand to rotate the nozzle. The nozzle, in all of the above mentioned syringe designs, is connected to the syringe so as to allow rotation of the nozzle. The above described nozzles are curved so that rotation of the nozzle in its connection with the syringe acts to change the exit path direction in relation to the handle of the syringe. In the design providing the above mentioned grasping means, that grasping means is a part of the mold for the nozzle. Any nozzle produced with that mold must include that grasping means. The grasping means cannot be offered as an option for the nozzle of that syringe. To provide a nozzle without that grasping means a seperate mold would be required. The grasping means cannot be taken from one syringe nozzle and placed on another syringe nozzle. The grasping means can only be utilized with the design it is incorporated into and molded with. If the grasping means is damaged the entire nozzle must be replaced. If the consumer desires the grasping means, the syringe model including that grasping means must be purchased. In many situations the syringe model including that grasping means will not be complimentary with other aspects of the consumers dental care facility. The grasping means cannot be obtained seperatly for use on any other syringe.

OBJECTS AND ADVANTAGES

Accordingly several objects and advantages of my invention are now disclosed. The present invention provides for a grasping means which is fabricated seperately from the nozzle described above. This allows the combination of the nozzle and grasping means to be temporary in nature if desired or permanent if this is desired. By fabricating the nozzle and grasping means seperately, the nozzle can be utilized without the grasping means, in situations where the grasping means is not wanted, without the necessity for duplicate nozzle molds or production facilities. In those instances where the grasping means is requested, it can be attached to the nozzle during construction and assembly or provided as an aftermarket addition to that nozzle. Permanent attachment of the grasping means to the nozzle can be accomplished by a variety of methods including adhesion, soldering, welding, overlaying of both the grasping means and the nozzle with an appropriate overlay material, or any other method of permanent combination. Temporary attachment of the grasping means to the nozzle can be accomplished by a variety of methods including frictional contact, physical engagement, or any other method of temporary combination. The present invention provides for a grasping means which if temporarily attached can be removed from one syringe nozzle and placed on another syringe nozzle, and which can be replaced without replacement of the nozzle. The present invention provides for a grasping means which can be utilized with any syringe mode even if that syringe was not designed to provide for unilateral control over the exit path direction. The present invention provides for a grasping means which can be obtained for use on existing syringe models, thereby providing the consumer with the ability to retain equipment presently in use and still obtain the benefits of unilateral control over the exit path direction.

Further objects and advantages of my invention will become apparent from a consideration of the drawings and ensuing description of the invention.

Figure 1:
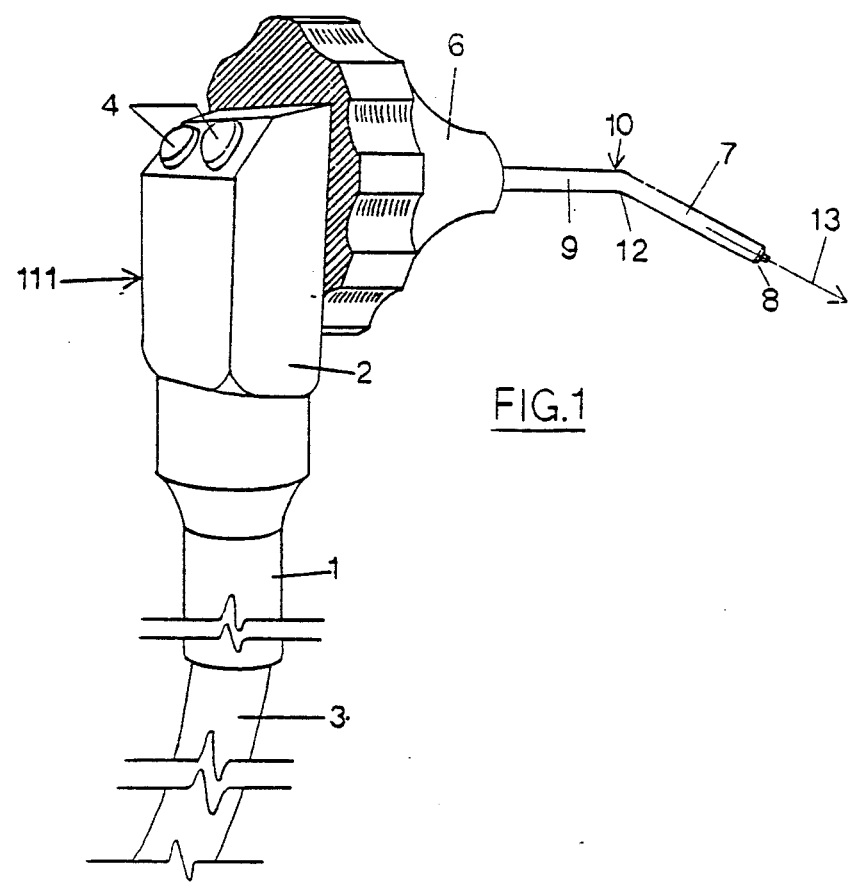
FIG. 1 is an external perspective view of a dental syringe of the type to which the present invention applies with the present invention diagrammatically included.
Figure 2:
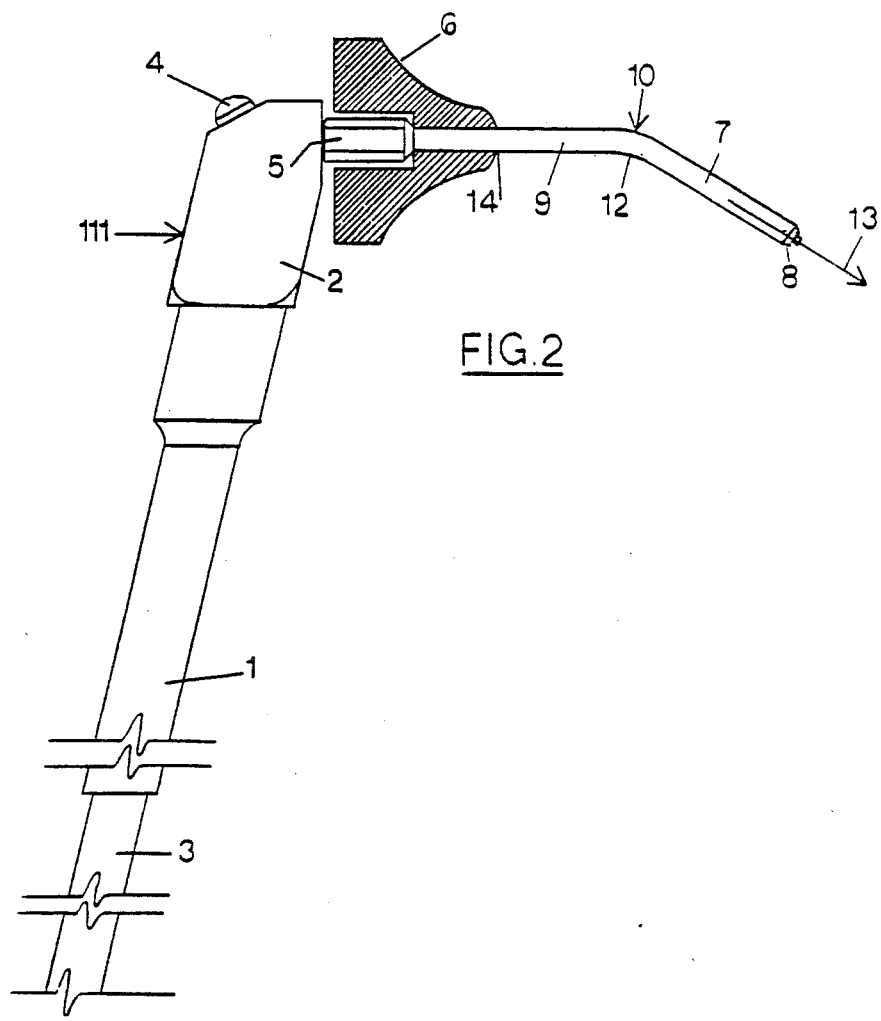
FIG. 2 is an exterior side view of a dental syringe of the type to which the present invention applies with a cross sectional view of the present invention shown diagrammatically.

LIST OF REFERENCE NUMERALS 1 handle of syringe
2 head of syringe
3 supply source of agents
4 agent control mechanisms
5 rotary connection of nozzle to syringe
6 grasping means
7 angled tip of nozzle
8 discharge orifice
9 shank of nozzle
10 nozzle
12 curved area of nozzle
13 exit path of agents
14 attachment of grasping means to nozzle
111 syringe

DESCRIPTION OF THE PREFERRED EMBODIMENTS

The principals of the present invention are useful when applied to a dental syringe generally indicated at 111. The syringe at 111 includes a handle 1 for the purpose of holding the syringe 111 during use, a head 2 which serves in combination with the handle 1 to encase the internal workings of the syringe 111, a supply 3 of the agents it directs and delivers, control mechanisms 4 for regulating the volume of and for selection of the agents, a connection 5 between the nozzle 10 and head 2 which allows rotation, a nozzle 10 which conducts the agents from the head 2 through the nozzle's shank 9 through the nozzle's curved portion 12 through the nozzle's angled tip 7 and on to exit from the nozzle's discharge orifice 8 along the agents exit path 13.

The nozzle 10 is attached to the head 2 by the rotary connection 5 so that rotation of the nozzle's shank 9 facilitates alteration of the direction of the agents exit path 13 in relation to the handle 1.

The present invention provides for rotation of the nozzle's shank 9 in the rotary connection 5 by placing a grasping means 6 on the nozzle 10. The grasping means 6 is designed for use by the hand holding and operating the syringe 111 while allowing that hand to remain in an operating position. The grasping means 6 is attached to the nozzle 10. The attachment of the grasping means 6 to the nozzle 10 is generally indicated at 14. The grasping means 6 is placed in close proximity to the head 2 of the syringe 111 and is designed and positioned for use by the hand holding and operating the syringe 111. The attachment 14 can be temporary or permanent.

As the grasping means 6 has attachment 14 to the nozzle 10, rotation of the grasping means 6 will cause rotation of the nozzle's shank 9 leading to a change in the direction of the exit path 13 in relation to the handle 1. The grasping means 6 will not interfere with dissasembly of the nozzle 10 from the head 2 and will allow sterilization by existing techniques.

OPERATION OF THE INVENTION

The present invention provides a grasping means to be attached to the nozzle of a dental syringe as described above. The grasping means allows the user of that syringe to control the direction of the exit path described above with the hand used to hold and operate that syringe. This direction control is accomplished by reaching forward with the thumb and forefinger of that hand to grasp and rotate the grasping means. This rotation of the grasping means causes rotation of the nozzle in its connection with the syringe which thereby redirects the exit path of the agents.

While the above description contains many specificities, the reader should not construe these as limitations on the scope of the invention, but merely as exemplifications of preferred embodiments thereof. Those skilled in the art will envision other possible variations within the scope of the invention.

For example, skilled artisans will be able to change the dimensions and shapes of the various embodiments. Furthermore, various methods of attachment may be employed between the grasping means and the nozzle. For example, attachment could be accomplished utilizing one or more set screws. Accordingly the reader is requested to determine the scope of this invention by the appended claims and their legal equivalents, and not by the examples which have been given.

I claim:

1. A dental syringe including a handle and a nozzle and means to rotate said nozzle with respect to said handle wherein:
    said syringe is used to direct and deliver controlled amounts of various agents including air and water,
    said nozzle is connected to said syringe so as to allow rotation of said nozzle,
    said means to rotate is for rotating said nozzle at said connection,
    said nozzle includes a discharge orifice for said agents,
    said agents depart said discharge orifice along an exit path, and wherein
    said rotation causes redirection of said exit path,
    said redirection is relative to said handle of said syringe,
    said means to rotate is provided for use by the hand which holds and operates said syringe, and wherein
    said means to rotate allows said hand to remain in an operating position while utilizing said means to rotate, and wherein
    a grasping means is provided to facilitate said means to rotate, and wherein
    said grasping means is removably attached to said nozzle,
    said grasping means being provided with means for preventing relative rotation between said nozzle and said grasping means whereby said grasping means and said nozzle rotate as a unit,
    said grasping means is of a size to allow operation by said hand, and wherein
    said grasping means has a design to prevent slipping of said hand during said rotation.

2. The invention of claim 1 wherein said grasping means is attached to said nozzle frictional contact.

3. The invention of claim 1 wherein said grasping means is attached to said nozzle utilizing an appropriate number of set screws.

* * * * *